(12) United States Patent
Wei et al.

(10) Patent No.: US 10,981,941 B2
(45) Date of Patent: Apr. 20, 2021

(54) METAL COMPLEX AS SENSOR COMPOUND FOR DETECTING GAS ANALYTE

(71) Applicant: CARRIER CORPORATION, Palm Beach Gardens, FL (US)

(72) Inventors: Alexander Wei, West Lafayette, IN (US); Aiganym Yermembetova, West Lafayette, IN (US); Benjamin M. Washer, Lafayette, IN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 0 days.

(21) Appl. No.: 16/811,678

(22) Filed: Mar. 6, 2020

(65) Prior Publication Data
US 2020/0291053 A1    Sep. 17, 2020

Related U.S. Application Data

(60) Provisional application No. 62/816,672, filed on Mar. 11, 2019.

(51) Int. Cl.
*C07F 19/00* (2006.01)
(52) U.S. Cl.
CPC ............................... *C07F 19/005* (2013.01)
(58) Field of Classification Search
CPC .................................................... C07F 19/00
See application file for complete search history.

(56) References Cited

U.S. PATENT DOCUMENTS

2013/0273665 A1    10/2013    Swager et al.
2015/0247832 A1    9/2015    Swager et al.

OTHER PUBLICATIONS

Ojo et al., 2001, caplus an 2001:153627.*
Reglinski et al., 1999, caplus an 1999:418573.*
Chen et al., "Selective Detection of Ethylene by MoS2—Carbon Nanotube Networks Coated with Cu(I)—Pincer Complexes", ACS Sensors,2020, No. 5, pp. 1699-1706.
Esser et al., "Selective Detection of Ethylene Gas Using Carbon Nanotube-based Devices: Utility in Determination of Fruit Ripeness", Agnew. Chem. Int. Ed. 2012, No. 51, pp. 5752-5756.
European Search Report for European Application No. 20162037.4; Application Filing Date: Mar. 10, 2020; dated Aug. 3, 2020, 7 pages.
Fu et al., "Ultrasensitive Ethene Detector Based on Graphene-Copper(I) Hybrid Material", Nano Lett. 2017, No. 17, pp. 7980-7988.
Ping et al., "Recent Advances in Sensing Applications of Two-Dimensional Transition Metal Dichalcogenide Nanosheets and Their Composites", Advanced Functional Materials, 2017, No. 27, 18 pages.

* cited by examiner

*Primary Examiner* — Sun Jae Yoo
(74) *Attorney, Agent, or Firm* — Cantor Colburn LLP

(57)    ABSTRACT

A sensor compound and sensor composition comprising the sensor compound are disclosed. The sensor compound includes a metal atom and a mercaptoimidazolyl multidentate ligand. The sensor composition comprises the sensor compound and a metal dichalcogenide.

9 Claims, No Drawings

METAL COMPLEX AS SENSOR COMPOUND FOR DETECTING GAS ANALYTE

CROSS REFERENCE TO RELATED APPLICATIONS

This application claims the benefit of U.S. Provisional Patent Application No. 62/816,672 filed on Mar. 11, 2019 which is incorporated by reference herein in its entirety.

BACKGROUND

Exemplary embodiments pertain to the art of sensor compositions based on metal complexes.

Volatile compounds with a double bond form an important group of compounds for detection. In particular, volatile alkenes, such as ethylene, are analytes of considerable importance. In particular, the detection of ethylene is important to industries related to produce and agriculture. Due to its small size and limited chemical functionality, however, ethylene is a challenging chemical analyte to detect. More efficient and sensitive methods of detection than those currently available are desired.

BRIEF DESCRIPTION

Disclosed is a sensor compound comprising a metal atom and a mercaptoimidazolyl multidentate ligand.

In addition to one or more of the features described above, or as an alternative to any of the foregoing embodiments, the metal atom is Cu(I), Ag(I) or Au(I).

In addition to one or more of the features described above, or as an alternative to any of the foregoing embodiments, the mercaptoimidazolyl multidentate ligand comprises more than one mercaptoimidazolyl group.

In addition to one or more of the features described above, or as an alternative to any of the foregoing embodiments, the mercaptoimidazolyl multidentate ligand further comprises a pyrazolyl group or an indolyl group.

In addition to one or more of the features described above, or as an alternative to any of the foregoing embodiments, the compound has formula (I)

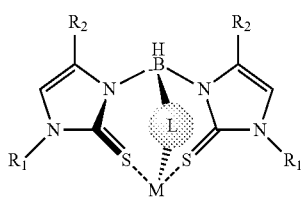

(I)

where each instance of $R_1$ and $R_2$ can be hydrogen, or a group having one or more carbons, M is Au(I), Ag(I) or Cu(I), and L is a pyrazolyl group, a mercaptoimidazolyl group, or an indolyl group.

In addition to one or more of the features described above, or as an alternative to any of the foregoing embodiments, the compound has formula II

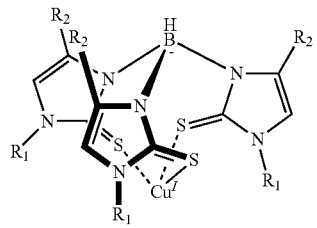

(II)

where each instance of $R_1$ and $R_2$ can be hydrogen, or a group having one or more carbons.

Also disclosed is a sensor composition comprising a sensor compound and a metal dichalcogenide, wherein the sensor compound comprises a metal atom and a mercaptoimidazolyl multidentate ligand.

In addition to one or more of the features described above, or as an alternative to any of the foregoing embodiments, the metal atom is Cu(I), Ag(I) or Au(I).

In addition to one or more of the features described above, or as an alternative to any of the foregoing embodiments, the mercaptoimidazolyl ligand comprises more than one mercaptoimidazolyl group.

In addition to one or more of the features described above, or as an alternative to any of the foregoing embodiments, the mercaptoimidazolyl ligand further comprises a pyrazolyl group or an indolyl group.

In addition to one or more of the features described above, or as an alternative to any of the foregoing embodiments, the sensor compound has formula (I)

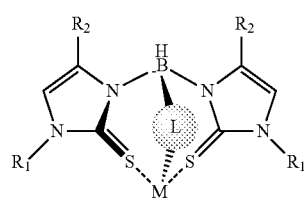

(I)

where each instance of $R_1$ and $R_2$ can be hydrogen, or a group having one or more carbons, M is Au, Ag or Cu, and L is a pyrazolyl group, a mercaptoimidazolyl group, or an indolyl.

In addition to one or more of the features described above, or as an alternative to any of the foregoing embodiments, the sensor compound has formula II

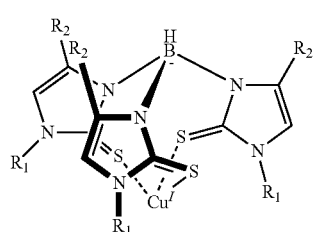

(II)

where each instance of $R_1$ and $R_2$ can be hydrogen, or a group having one or more carbons.

In addition to one or more of the features described above, or as an alternative to any of the foregoing embodiments, the metal dichalcogenide comprises $MoS_2$, $WS_2$, $MoSe_2$, $WSe_2$, $MoTe_2$, $WTe_2$, and combinations thereof.

DETAILED DESCRIPTION

A detailed description of one or more embodiments of the disclosed apparatus and method are presented herein by way of exemplification and not limitation.

Volatile compounds with a double or triple bond is a group of important compounds for detecting and monitoring. The term volatile, as used herein, refers to compounds that are in the gas phase at standard temperature and pressure. Exemplary compounds include $NO_2$, $CO_2$, $CO$, and alkenes such as $C_2H_4$ (ethylene). As the hormone responsible for initiating the ripening of fruit as well as other processes in plant development, ethylene is an analyte of considerable importance to industries related to produce and agriculture. Due to its small size and limited chemical functionality, ethylene and other volatile alkenes are challenging chemicals to detect. Disclosed herein is a sensor compound and a sensor composition capable of detecting volatile compounds with a double or triple bond such as ethylene and other volatile alkenes. These compounds can be detected at levels down to 100 parts per billion (ppb).

The sensor compound comprises a metal atom and a multidentate mercaptoimidazolyl ligand, which combine to form a multidentate metal-ligand coordination complex. The mercaptoimidazolyl ligand comprises at least one mercaptoimidazolyl groups which coordinates to the metal atom through the sulfur atoms. In addition to the mercaptoimidazolyl group(s) the ligand may further comprise a pyrazolyl group, an indolyl group, or a combination thereof, which can be referred to as a heteroleptic ligand. If the mercaptoimidazolyl ligand comprises only mercaptoimidazolyl groups it can be referred to as a homoleptic ligand. The sensor compound may have formula (I)

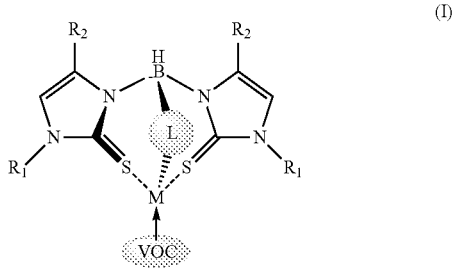

(I)

where each instance of $R_1$ and $R_2$ can be hydrogen or a group containing one more carbon atoms. In some embodiments each instance of $R_1$ and $R_2$ can be hydrogen or an alkyl group having 1 to 5 carbons. L in formula (I) can be a pyrazolyl group, a mercaptoimidazolyl group, or an indolyl group. VOC in formula I is present to show a postulated interaction with the volatile compound having a π bond. Without being bound by theory it is believed that the π bond of the volatile compound coordinates with an empty coordination site on the metal-ligand complex. The coordination alters the electronic configuration of the complex and can impact the electrical properties of the metal-ligand complex.

A more specific example of a mercaptoimidazolyl metal-ligand complex is shown in formula (II).

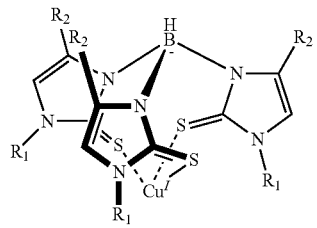

(II)

In formula (II) there are three mercaptoimidazolyl groups. $R_1$ and $R_2$ are defined as in formula (I).

The metal atom in the mercaptoimidazolyl metal-ligand complex may be a Group 11 element such as Cu(I), Ag(I), or Au(I).

The sensor compound (or sensor compounds) may be combined with a metal dichalcogenides to form a sensor composition. Metal dichalcogenides include transition metal dichalcogenides which are compounds formed from a 6B Group metal and a chalcogenide (S, Se, and Te). Exemplary metal dichalcogenides include $MoS_2$, $WS_2$, $MoSe_2$, $WSe_2$, $MoTe_2$, $WTe_2$, and combinations thereof. The metal dichalcogenide is in the form of nanosized particles. "Nanosized" as it applies to the metal dichalcogenides refers to the fact that the particles have at least one dimension that is less than or equal to 100 nanometers. The metal dichalcogenides are typically available in a flake form with a thickness of 100 nanometers or less although other physical forms are not excluded such as few-layer or single-layer materials, with the caveat that the physical form has at least one linear dimension that is less than or equal to 100 nanometers.

The sensor compound and metal dichalcogenide interact and when the volatile compound is bound to the sensor compound the electrical properties of the sensor composition change—either by increasing the conductivity or the resistivity. The change in electrical property is consistent and predictable, allowing reliable detection of the target volatile compound.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A sensor compound comprising a metal atom and a mercaptoimidazolyl multidentate ligand, wherein the mercaptoimidazolyl multidentate ligand comprises a pyrazolyl group or an indolyl group.

2. The sensor compound of claim 1, wherein the metal atom is Cu(I), Ag(I) or Au(I).

3. The sensor compound of claim 1, wherein the compound has formula (I)

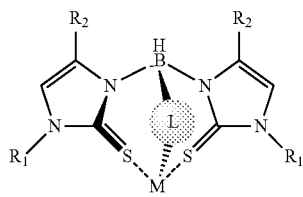

(I)

where each instance of $R_1$ and $R_2$ can be hydrogen, or a group having one or more carbons, M is Au(I), Ag(I) or Cu(I), and L is a pyrazolyl group or an indolyl group.

4. A sensor composition comprising a sensor compound and a metal dichalcogenide wherein the sensor compound comprises a metal atom and a mercaptoimidazolyl multidentate ligand.

5. The sensor composition of claim 4, wherein the metal atom is Cu(I), Ag(I) or Au(I).

6. The sensor composition of claim 4, wherein the mercaptoimidazolyl ligand further comprises a pyrazolyl group or an indolyl group.

7. The sensor composition of claim 4, wherein the sensor compound has formula (I)

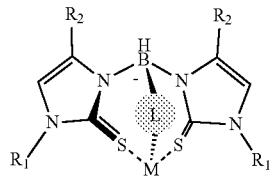

(I)

where each instance of $R_1$ and $R_2$ can be hydrogen, or a group having one or more carbons, M is Au, Ag or Cu, and L is a pyrazolyl group, a mercaptoimidazolyl group, or an indolyl group.

8. The sensor composition of claim 4, wherein the sensor compound has formula II

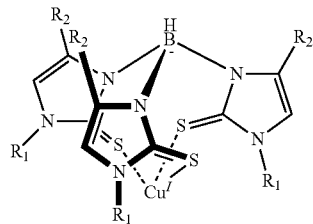

(II)

where each instance of $R_1$ and $R_2$ can be hydrogen, or a group having one or more carbons.

9. The sensor composition of claim 4, wherein the metal dichalcogenide comprises $MoS_2$, $WS_2$, $MoSe_2$, $WSe_2$, $MoTe_2$, $WTe_2$, and combinations thereof.

* * * * *